(12) United States Patent
Castillo

(10) Patent No.: US 7,892,995 B2
(45) Date of Patent: *Feb. 22, 2011

(54) LITHIUM SILICATE GLASS CERAMIC AND METHOD FOR FABRICATION OF DENTAL APPLIANCES

(75) Inventor: Rodolfo Castillo, Boca Raton, FL (US)

(73) Assignee: James R. Glidewell Dental Ceramics, Inc.

( * ) Notice: Subject to any disclaimer, the term of this patent is extended or adjusted under 35 U.S.C. 154(b) by 102 days.

This patent is subject to a terminal disclaimer.

(21) Appl. No.: 12/283,472

(22) Filed: Sep. 12, 2008

(65) Prior Publication Data

US 2009/0256274 A1 Oct. 15, 2009

Related U.S. Application Data

(63) Continuation-in-part of application No. 12/082,576, filed on Apr. 11, 2008, now abandoned.

(51) Int. Cl.
*C03C 10/04* (2006.01)

(52) U.S. Cl. ............................................. 501/5; 106/35

(58) Field of Classification Search ..................... 501/5; 106/35
See application file for complete search history.

(56) References Cited

U.S. PATENT DOCUMENTS

| | | | | |
|---|---|---|---|---|
| 5,698,019 A * | 12/1997 | Frank et al. | .................... | 106/35 |
| 6,342,458 B1 * | 1/2002 | Schweiger et al. | .............. | 501/5 |
| 6,455,451 B1 * | 9/2002 | Brodkin et al. | ................. | 501/5 |
| 7,381,258 B2 * | 6/2008 | Krumbholz | ................... | 106/35 |
| 2005/0155518 A1* | 7/2005 | Krumbholz | ................... | 106/35 |
| 2005/0288165 A1* | 12/2005 | Krumbholz | ..................... | 501/6 |

* cited by examiner

*Primary Examiner*—Karl E Group
(74) *Attorney, Agent, or Firm*—Leonard Tachner

(57) ABSTRACT

The present invention relates to preparing an improved lithium silicate glass ceramic for the manufacture of blocks for dental appliance fabrication using a CAD/CAM process. The lithium silicate material has a chemical composition that is different from those reported in the prior art including 8 to 10% of germanium dioxide in the final composition. The softening points are close to the crystallization final temperature of 830° C. indicating that the samples will support the temperature process without shape deformation. The resulting material has improved castability and higher density.

4 Claims, 2 Drawing Sheets

LITHIUM SILICATE GLASS CERAMIC AND METHOD FOR FABRICATION OF DENTAL APPLIANCES

CROSS-REFERENCE TO RELATED APPLICATIONS

This application is a continuation-in-part of application Ser. No. 12/082,576, filed on Apr. 11, 2008 now abandoned.

BACKGROUND OF THE INVENTION

1. Field of the Invention

The present invention relates to a lithium silicate glass ceramic material for the manufacturing of blocks and subsequent fabrication of single dental crowns with the aid of the CAD/CAM process. The invention relates to an improved version of such glass ceramic containing germanium dioxide to make it more castable with higher density and higher flexural strength than the lithium disilicate free of germanium dioxide.

2. Background Art

There are many products available in the market employing lithium disilicate material and covered by several U.S. patents. Some of these patents claim a process for the preparation of shaped translucent lithium disilicate glass ceramic products from a mixture of basic components ($SiO_2$, $Al_2O_3$, $K_2O$, $Li_2O$, plus pigments and fluorescent oxides). The addition of lanthanum oxide results in a product with excellent dimensional stability on heating. Other patents describe the process for the production of lithium disilicate glass ceramic where mixtures of basic components except lanthanum oxide are claimed in different ranges. A patent also describes a lithium disilicate preparation which uses zirconium, titanium dioxide and phosphorus as nucleation agents in their formulation. There are also some other patents, scientific papers and technical books describing the preparation methods of lithium disilicate glass ceramic. Most of them use similar composition ranges of the patents described above and the thermal cycles of nucleation and crystallization.

Most of the existing patents in the dental field use the same basic components. The present invention uses germanium dioxide as a fundamental part of the formula. This oxide is broadly used in glass preparation for its good optical properties. The oxide has been well studied and has positive effects compared to common silicon glasses. It has been found that the addition of germanium oxide produces a melt with low viscosity facilitating the castability of the process and increases the thermal expansion and the refractive index of the resulting lithium silicate glass ceramic. More important, the addition of germanium dioxide increases the final density of the glass resulting in higher values of flexural strength than the lithium disilicate glasses free of germanium dioxide. Because the final composition of this invention uses a molar ratio of Si/Li between 1.8 and 1.9, only Lithium Silicate, instead of Lithium Di Silicate, is present as the main constituent of the crystalline phase after full crystallization of the glass ceramic.

SUMMARY OF THE INVENTION

The present invention relates to preparing an improved lithium silicate glass ceramic for the manufacture of blocks for dental appliance fabrication using a CAD/CAM process. The lithium silicate material has a chemical composition that is different from those reported in the prior art, especially because of the use of germanium dioxide in the formulas and its low silicon dioxide content. The softening points are close to the crystallization final temperature of 800° C. indicating that the samples will support the temperature process without shape deformation.

The initial components are chemical precursors, specifically aluminum hydroxide for the aluminum oxide, boric acid for the boron oxide, lithium carbonate for lithium oxide, di-hydrogen phosphate or tri-calcium phosphate for phosphorus pentoxide, zirconium silicate or yttrium stabilized zirconia for zirconium oxide, and potassium carbonate for potassium oxide. The remaining elements are single oxides precursors of silicon, cerium, titanium, erbium, vanadium, germanium, samarium, dysprosium, terbium, europium, tantalum, and manganese oxides.

The components are mixed for about 10 to 15 minutes in a blender. Then the mixture is put into an alumina jar ball mill using zirconia balls as a grinding media and ground for about one to two hours. This step is essential for optimizing the blend of materials especially when the precursors used have different particle sizes. The ball mill process can be done wet or dry depending on the chemistry of precursors used. One embodiment uses 2-propanol, n-hexane and ethanol as solvents. Once the solvent is removed from the powder by filtration and evaporation, the powder is placed inside a platinum crucible and heated from room temperature to 1400° to 1500° C. for 1 to 3 hours. Then the melt is cast into rectangular or cylindrical graphite molds and the resulting blocks are cooled down to room temperature. Because of the wet or dry mill process step there is no need for a second re-melting process for improving homogeneity.

BRIEF DESCRIPTION OF THE DRAWINGS

The aforementioned objects and advantages of the present invention, as well as additional objects and advantages thereof, will be more fully understood herein after as a result of a detailed description of a preferred embodiment when taken in conjunction with the following drawing in which.

DETAILED DESCRIPTION OF PREFERRED EMBODIMENTS

Figure 1:
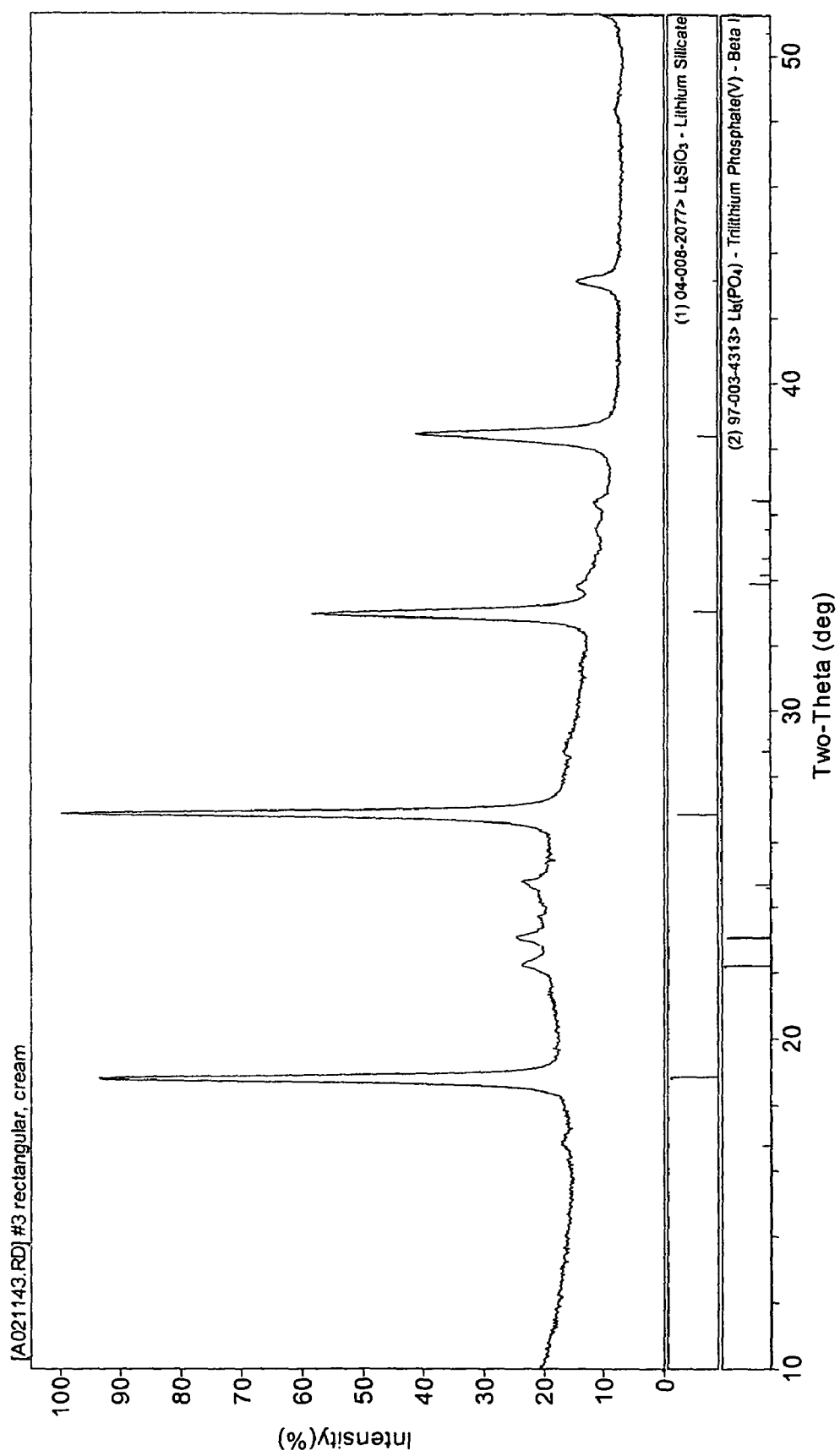
FIG. 1 is an XRD diffraction pattern of a sample of this invention after crystallization showing the presence of lithium silicate as a main constituent phase in the glass ceramic composition. Because the molar ratio of Si/Li is between of 1.8 to 1.9 the crystallized phase of the final material only shows the presence of Lithium Silicate instead of Lithium Di Silicate.
Figure 2:
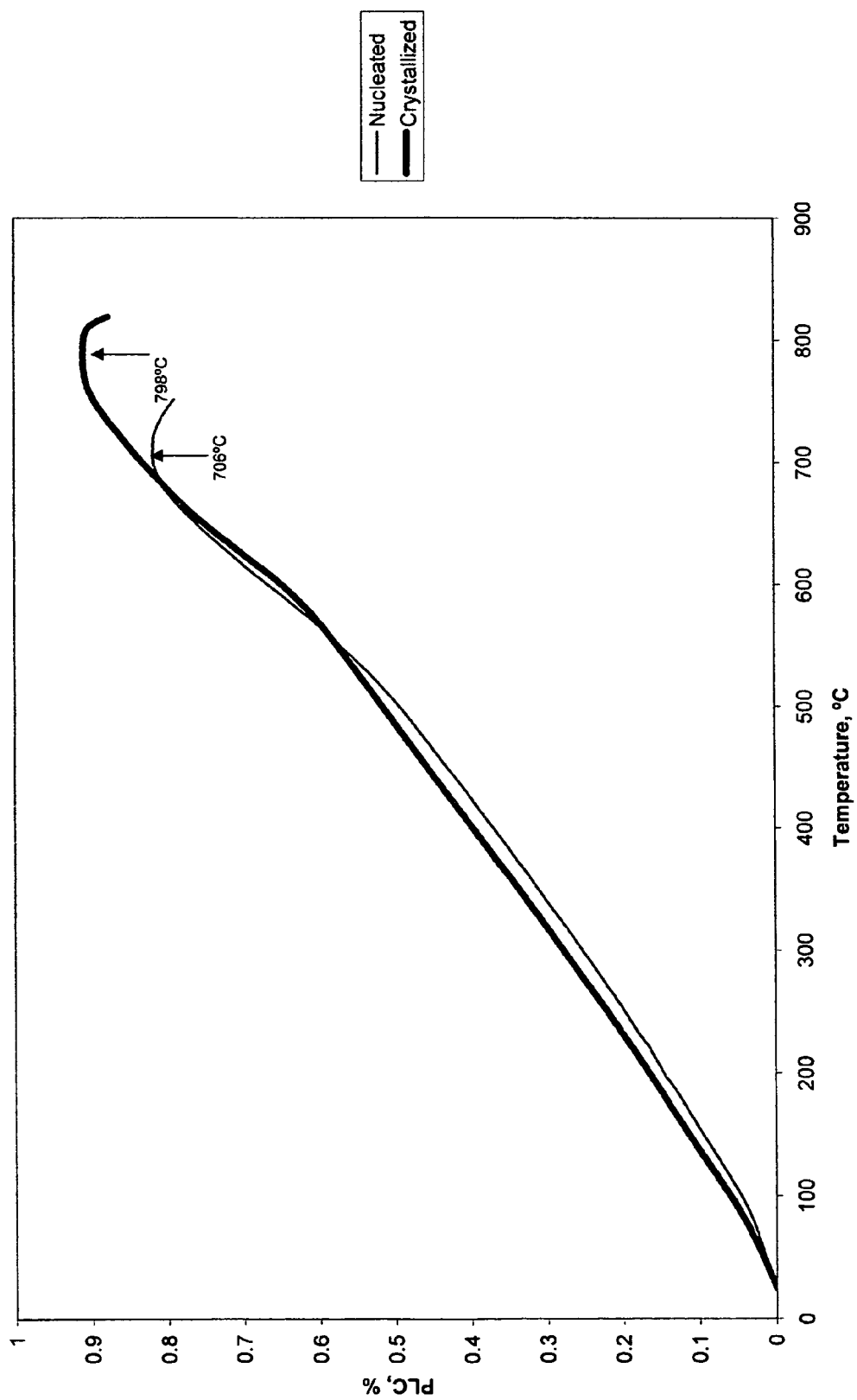
FIG. 2, is a graphical illustration of a dilatometric measurement of a sample of the invention resulting from full crystallization.

The prior art materials are based on the formation of lithium disilicate materials. Therefore, an object of the present invention is to prepare a controlled nucleated lithium metasilicate or lithium silicate glass ceramic with excellent machining properties. Then by heat treatment, a complete crystal growth is achieved forming a glass ceramic product with outstanding mechanical properties, excellent optical properties, very good chemical solubility, little contraction and high flexural strength. Applicant found that the use of germanium oxide creates several advantages for this formula and process compared to existing lithium disilicate materials. One such advantage is a low viscosity of the melt during the firing process that improves the castability of the material. Another advantage is a higher final density (10% higher than regular lithium disilicate material) that improves flexural strength and the final translucency is almost as good as that of the $GeO_2$ free glass ceramic.

The lithium silicate of the present invention comprises the following components and compositions:

TABLE I

| COMPONENT | MIN | MAX |
|---|---|---|
| $SiO_2$ | 53.0 | 59.0 |
| $Al_2O_3$ | 2.5 | 3.4 |
| $K_2O$ | 3.5 | 4.1 |
| $CeO_2$ | 0 | 2.0 |
| $Li_2O$ | 14.0 | 16.0 |
| $ZrO_2$ | 2.5 | 6.0 |
| $TiO_2$ | 0.5 | 1.8 |
| $P_2O_5$ | 2.7 | 4.0 |
| $Er_2O_3$ | 0 | 2.0 |
| $V_2O_5$ | 0 | 1.0 |
| $GeO_2$ | 0 | 8.4 |
| $MnO_2$ | 0 | 1.0 |
| $Tb_4O_7$ | 0 | 2.0 |
| $Ta_2O_5$ | 0 | 1.0 |
| $Dy_2O_3$ | 0 | 1.0 |
| $Pr_2O_3$ | 0 | 1.0 |
| $Sm_2O_3$ | 0 | 6.0 |
| $Eu_2O_3$ | 0 | 1.0 |

The invention is explained in more detail below with the following examples:

The preparation of numerous sample and elemental oxide composition of each are listed in the Table II.

TABLE II

| | \multicolumn{8}{c}{Components % weight.} | | | | | | | |
| | TEST #1 | TEST #2 | TEST #3 | TEST #4 | TEST #5 | TEST #6 | TEST #7 | TEST #8 |
|---|---|---|---|---|---|---|---|---|
| $SiO_2$ | 56.4 | 57.9 | 56.5 | 55.9 | 55.9 | 56.1 | 56.1 | 55.9 |
| $Al_2O_3$ | 3.3 | 3.2 | 3.3 | 3.2 | 3.2 | 3.2 | 3.2 | 3.2 |
| $K_2O$ | 3.6 | 4.1 | 3.6 | 3.6 | 3.6 | 3.6 | 3.6 | 3.6 |
| $CeO_2$ | 0.9 | 1.8 | 0.9 | 0.9 | 0.9 | 0.9 | 0.9 | 0.9 |
| MgO | | | | | | | | |
| $Li_2O$ | 15.5 | 12.4 | 15.5 | 15.3 | 15.3 | 15.4 | 15.4 | 15.3 |
| ZnO | | 2.4 | | | | | | |
| $ZrO_2$ | 5.1 | 2.5 | 5.1 | 5.1 | 5.1 | 5.1 | 5.1 | 5.1 |
| $TiO_2$ | 0.6 | 0.6 | 0.6 | 0.6 | 0.6 | 0.6 | 0.6 | 0.6 |
| $P_2O_5$ | 3.1 | 3.7 | 3.1 | 3.0 | 3.0 | 3.1 | 3.1 | 3.0 |
| $Er_2O_3$ | 0.1 | 0.4 | 0.6 | 0.5 | 0.5 | 0.5 | 0.5 | 0.3 |
| $V_2O_5$ | 0.1 | 0.1 | 0.1 | 0.1 | 0.1 | 0.1 | 0.1 | 0.3 |
| $GeO_2$ | 8.1 | 7.8 | 8.1 | 8.0 | 8.0 | 8.1 | 8.1 | 8.0 |
| $MnO_2$ | | | | | | | | |
| $Tb_4O_7$ | | | | 0.5 | 0.5 | 1.3 | 1.3 | 0.0 |
| $Pr_2O_3$ | | | | | | | | |
| $Sm_2O_3$ | 3.2 | 3.1 | 2.6 | 3.2 | 3.2 | 1.9 | 1.9 | 3.8 |

| | TEST #9 | TEST #10 | TEST #11 | TEST #12 | TEST #13 | TEST #14 | TEST #15 | TEST #16 |
|---|---|---|---|---|---|---|---|---|
| $SiO_2$ | 55.9 | 55.6 | 55.9 | 55.8 | 55.9 | 55.9 | 55.8 | 55.8 |
| $Al_2O_3$ | 3.2 | 3.0 | 3.2 | 3.2 | 3.2 | 3.2 | 3.2 | 3.2 |
| $K_2O$ | 3.6 | 3.6 | 3.6 | 3.6 | 3.6 | 3.6 | 3.6 | 3.6 |
| $CeO_2$ | 0.9 | 0.9 | 0.9 | 0.9 | 0.9 | 0.9 | 0.9 | 0.9 |
| MgO | | | | | | | | |
| $Li_2O$ | 15.3 | 15.3 | 15.3 | 15.3 | 15.3 | 15.3 | 15.3 | 15.3 |
| ZnO | | | | | | | | |
| $ZrO_2$ | 5.1 | 6.0 | 5.1 | 5.1 | 5.1 | 5.1 | 5.1 | 5.1 |
| $TiO_2$ | 0.6 | 0.6 | 0.6 | 0.6 | 0.6 | 0.6 | 0.6 | 0.6 |
| $P_2O_5$ | 3.0 | 2.7 | 3.0 | 3.0 | 3.0 | 3.0 | 3.0 | 3.0 |
| $Er_2O_3$ | 0.3 | | | | 0.0 | 0.0 | 0.1 | 0.1 |
| $V_2O_5$ | 0.3 | | | 0.1 | 0.0 | 0.0 | | 0.1 |
| $GeO_2$ | 8.0 | 8.0 | 8.0 | 8.0 | 8.0 | 8.0 | 8.0 | 8.0 |
| $MnO_2$ | | | | | | | | |
| $Tb_4O_7$ | 0.0 | | | | | | 0.1 | |
| $Pr_2O_3$ | | | | | | | | |
| $Sm_2O_3$ | 3.8 | 4.4 | 4.3 | 4.3 | 4.3 | 4.3 | 4.3 | 4.3 |

| | TEST #17 | TEST #18 | TEST #19 | TEST #20 | TEST #21 | TEST #22 | TEST #23 |
|---|---|---|---|---|---|---|---|
| $SiO_2$ | 55.7 | 55.8 | 56.0 | 58.2 | 55.6 | 54.3 | 57.7 |
| $Al_2O_3$ | 3.2 | 3.2 | 3.2 | 3.4 | 3.2 | 2.5 | 3.3 |
| $K_2O$ | 3.6 | 3.6 | 3.9 | 3.7 | 3.6 | 3.5 | 3.7 |
| $CeO_2$ | 0.9 | 0.9 | | 0.9 | 0.8 | | 1.0 |
| MgO | | | | | | 1.2 | |
| $Li_2O$ | 15.3 | 15.3 | 15.4 | 16.0 | 15.3 | 14.4 | 15.9 |
| ZnO | | | | | | 1.2 | |
| $ZrO_2$ | 5.1 | 5.1 | 5.1 | 5.3 | 5.0 | 4.9 | 5.2 |
| $TiO_2$ | 0.6 | 0.6 | 0.6 | 0.6 | 0.6 | 1.8 | 0.6 |
| $P_2O_5$ | 3.0 | 3.0 | 3.3 | 3.2 | 3.0 | 3.9 | 3.1 |
| $Er_2O_3$ | 0.3 | | | | | 0.1 | 0.3 |
| $V_2O_5$ | | 0.1 | 0.1 | 0.5 | 0.4 | 0.1 | 0.2 |
| $GeO_2$ | 8.0 | 8.0 | 8.1 | 8.4 | 8.0 | 7.8 | 8.3 |
| $MnO_2$ | | | | | | 0.1 | 0.2 |
| $Tb_4O_7$ | | | | | | | 0.4 |
| $Pr_2O_3$ | | | | | | | |
| $Sm_2O_3$ | 4.3 | 4.3 | 4.3 | | | 4.4 | 4.3 |

| | TEST #24 | TEST #25 | TEST #26 | TEST #27 | TEST #28 | TEST #29 | TEST #30 |
|---|---|---|---|---|---|---|---|
| $SiO_2$ | 56.6 | 55.3 | 54.2 | 53.9 | 53.9 | 54.1 | 54.5 | 54.3 |
| $Al_2O_3$ | 3.3 | 3.2 | 3.1 | 3.1 | 3.1 | 3.1 | 3.9 | 3.8 |
| $K_2O$ | 3.6 | 3.5 | 3.5 | 3.4 | 3.4 | 3.5 | 4.2 | 4.2 |
| $CeO_2$ | 0.9 | 0.9 | 0.6 | 0.6 | 0.6 | 1.0 | 0.6 | 0.6 |
| MgO | | | | | | | | |
| $Li_2O$ | 15.5 | 15.2 | 14.9 | 14.8 | 14.8 | 14.9 | 15.2 | 15.2 |
| ZnO | | | | | | | | |
| $ZrO_2$ | 5.1 | 5.0 | 4.9 | 4.9 | 4.9 | 4.9 | 4.9 | 4.9 |
| $TiO_2$ | 0.6 | 1.7 | 0.6 | 0.6 | 0.6 | 0.6 | 0.6 | 0.6 |
| $P_2O_5$ | 3.1 | 3.0 | 3.0 | 2.9 | 2.9 | 3.0 | 3.0 | 3.0 |
| $Er_2O_3$ | 0.1 | 0.1 | 0.4 | 1.0 | 1.3 | 1.5 | 1.3 | 1.3 |
| $V_2O_5$ | 0.10 | 0.05 | 0.03 | 0.03 | 0.03 | 0.06 | 0.04 | 0.03 |
| $GeO_2$ | 8.1 | 8.0 | 7.8 | 7.8 | 7.8 | 7.8 | 7.7 | 7.7 |
| $MnO_2$ | 0.1 | 0.1 | | | 0.0 | | | |
| $Tb_4O_7$ | 0.2 | 0.1 | | | | | | |
| $Pr_2O_3$ | | | 1.3 | 1.3 | 0.9 | 0.9 | 0.7 | 1.0 |
| $Sm_2O_3$ | 2.6 | 3.8 | 5.7 | 5.7 | 5.7 | 4.8 | 3.3 | 3.3 |

A lithium silicate material as described in Table I is particularly preferred which comprises 53 to 59 wt % of $SiO_2$, 14 to 19% wt of $Li_2O$ and 7 to 9% of $GeO_2$, where after nucleation only lithium silicate is formed and then after complete crystallization only lithium silicate crystals are formed.

The lithium silicate material of a preferred embodiment is produced by a process which comprises the following steps:

(a) A mix of the precursors of the final components are blended together for 10 to 15 min until a mechanical mix is obtained.

(b) The mix is ball milled dry or wet using zirconia media for about 1 to 2 hours to homogenize the components and achieve almost the same particle size in all the components.

(c) The sample is melted for about 1 to 3 hours at a temperature of 1400° to 1500° C.

(d) The melt is poured in cylindrical or rectangular graphite molds and let cool down to room temperature.

(e) The glass is subjected to a crystal nucleation process at a temperature of 625 to 650° C. for 10 to 60 min and the growth of the lithium silicate crystals are stopped temporally by cooling the glass ceramic to room temperature.

(f) The dental restoration is made using the previous nucleated glass block using a CAD-CAM milling device and then finally fully crystallized at a temperature of 760° to 830° C.

The coloring of the glass ceramic is obtained by mixing the rare earth oxides in specific amounts for obtaining highly esthetic dental restorations.

Coefficient of Thermal Expansion and Softening Point

The percentage linear change vs. temperature was measured using an Orton dilatometer and the coefficient of expansion at 500° C. and the softening point were calculated for all the samples. For this purpose a rectangular rod approximately 2 inches long was cast and then nucleated at 625° C. for 30 min. After this process the rod is cut in two parts. One part is used for measuring transition temperature, softening point temperature and coefficient of expansion of the nucleated phase. The second part is fully crystallized at 830° C. for about 30 minutes and is used for measuring the same properties. It is expected that after the crystallization step, the samples increase the softening temperature point. Coefficient of thermal expansion values for the crystallized state and softening point values for both the nucleated and crystallized states are shown for various samples in Table III.

Flexural Strength

Three point flexural strength tests (MPa) were performed on nucleated and crystallized samples. Flexural strength values are shown for various samples in Table III.

Chemical Solubility

A chemical solubility test was performed according to ISO-9693. Ten disc samples are placed in a flask glass with an aqueous solution of 4% (V/V) of acetic acid analytical grade (Alfa Aesar). The flask is heated at 80+/−3— for 16 h. The weight change before and after the test is determined and then the chemical solubility expressed as $\mu g/cm^2$ is calculated and shown in Table III.

TABLE III

|  | TEST #3 | TEST #19 | TEST #23 | TEST #25 |
|---|---|---|---|---|
| Softening temperature, ° C., nucleated sample | 702 | 739 | 766 | 762 |
| Softening temperature, ° C., crystallized sample | 826 | 810 | 789 | 794 |
| Coefficient of expansion, ×10⁻⁶/° C. Crystallized sample | 9.2 | 11.7 | 11.3 | 11.6 |
| Flexural strength, MPa, Nucleated sample | 137 | 113 | 99 | 99 |
| Flexural strength, MPa Crystallized sample | 310 | 340 | 320 | 305 |
| Chemical Solubility, $\mu g/cm^2$ Crystallized sample. | 48 | 66 | 39 | 11 |

The present invention relates to preparing a lithium silicate glass ceramic for the manufacture of blocks for dental appliance fabrication using a CAD/CAM process. The lithium silicate material has a chemical composition that is different from those reported in the prior art, especially because of the use of germanium dioxide in the formulas and the presence of lithium silicate instead of lithium disilicate in the full crystallized samples. The softening points are close to the crystallization final temperature of 830° C. indicating that the samples will support the temperature process without shape deformation.

It was found that the use of germanium creates several advantages for this new formula and process compared to existing lithium disilicate materials:

One such advantage is a low viscosity of the melt during the firing process which improves the castability of the material.

Another advantage is a higher final density at least 10% higher than regular lithium disilicate material which improves flexural strength.

Another advantage is the material has more radiopacity than the material free of germanium oxide facilitating the radiographic diagnosis of the restoration.

The preferred range composition (in % wt) of this glass ceramic material is the following:

TABLE IV

Preferred Range of Composition Components

| COMPONENT | MIN | MAX |
|---|---|---|
| $SiO_2$ | 54.3 | 58.2 |
| $Al_2O_3$ | 2.5 | 3.9 |
| $K_2O$ | 3.5 | 4.2 |
| $CeO_2$ | 0.8 | 1.8 |
| $MgO$ | 0.0 | 1.2 |
| $Li_2O$ | 12.4 | 16.0 |
| $ZnO$ | 1.2 | 2.4 |
| $ZrO_2$ | 2.5 | 6.0 |
| $TiO_2$ | 0.6 | 1.8 |
| $P_2O_5$ | 2.7 | 3.9 |
| $Er_2O_3$ | 0.0 | 1.5 |
| $V_2O_5$ | 0.0 | 0.5 |
| $GeO_2$ | 7.8 | 8.4 |
| $MnO_2$ | 0.0 | 0.2 |
| $Tb_4O_7$ | 0.0 | 1.3 |
| $Ta_2O_5$ | 0.0 | 0.0 |
| $Dy_2O_3$ | 0.0 | 0.0 |
| $Pr_2O_3$ | 0.0 | 1.3 |
| $Sm_2O_3$ | 0.0 | 5.7 |
| $Eu_2O_3$ | 0.0 | 1.0 |

One preferred example of this material has the following specific composition:

TABLE V

PREFERRED COMPOSITION

| Component | Weight % |
|---|---|
| $SiO_2$ | 54.3 |
| $Li_2O$ | 15.2 |
| $GeO_2$ | 7.67 |
| $Al_2O_3$ | 3.84 |
| $K_2O$ | 4.18 |
| $P_2O_5$ | 2.96 |
| $B_2O_3$ | 1.46 |
| $CaO$ | 0.73 |
| $TiO_2$ | 0.64 |
| $ZrO_2$ | 4.86 |
| $CeO_2$ | 0.64 |
| $Er_2O_3$ | 1.28 |
| $V_2O_5$ | 0.05 |
| $Sm_2O_3$ | 3.33 |
| $Pr_2O_3$ | 1.02 |

Having thus disclosed a number of embodiments of the formulation of the present invention, including a preferred range of components and a preferred formula thereof, those having skill in the relevant arts will now perceive various modifications and additions. Therefore, the scope hereof is to be limited only by the appended claims and their equivalents.

We claim:

1. A lithium silicate ceramic glass made from a composition mixture comprising:

about 54.3% wt $SiO_2$;

about 15.2% wt $Li_2O$; and about 7.6% wt $GeO_2$.

2. The lithium silicate ceramic glass recited in claim 1 wherein said composition mixture also comprises at least 1.9% wt of each of $Al_2O_3$, $K_2O$, $P_2O_5$, $ZrO_2$, $CeO_2$, $Pr_2O_3$ and $Sm_2O_3$.

3. The lithium silicate ceramic glass recited in claim 2 further comprising one or more of the following additional components $TiO_2$, $Er_2O_3$ and $V_2O_5$.

4. A Lithium silicate material recited in claim 3 wherein the lithium silicate crystals form 50 to 60 vol % of the lithium silicate material.

* * * * *